(12) United States Patent
Lerebour et al.

(10) Patent No.: US 11,020,332 B2
(45) Date of Patent: Jun. 1, 2021

(54) ACHILLEA ESSENTIAL OIL, COSMETIC COMPOSITION COMPRISING IT AND ITS USES

(71) Applicant: L'OREAL, Paris (FR)

(72) Inventors: Geraldine Lerebour, Les Loges (FR); Pierre Lartaud, Eurre (FR); Bertrand Lacroix, Villejuif (FR)

(73) Assignee: L'OREAL, Paris (FR)

( * ) Notice: Subject to any disclaimer, the term of this patent is extended or adjusted under 35 U.S.C. 154(b) by 352 days.

(21) Appl. No.: 14/395,224

(22) PCT Filed: Mar. 29, 2013

(86) PCT No.: PCT/EP2013/056828
§ 371 (c)(1),
(2) Date: Oct. 17, 2014

(87) PCT Pub. No.: WO2013/160066
PCT Pub. Date: Oct. 31, 2013

(65) Prior Publication Data
US 2015/0086498 A1 Mar. 26, 2015

Related U.S. Application Data

(60) Provisional application No. 61/727,142, filed on Nov. 16, 2012, provisional application No. 61/645,878, filed on May 11, 2012.

(30) Foreign Application Priority Data

Apr. 25, 2012 (FR) ...................................... 1253815
Jul. 17, 2012 (FR) ...................................... 1256877

(51) Int. Cl.
| | | |
|---|---|---|
| A61K 36/00 | (2006.01) | |
| A61K 8/35 | (2006.01) | |
| A61Q 5/00 | (2006.01) | |
| A61Q 15/00 | (2006.01) | |
| A61K 8/92 | (2006.01) | |
| A61K 8/38 | (2006.01) | |
| C11B 9/00 | (2006.01) | |
| A61K 8/31 | (2006.01) | |
| A61K 8/34 | (2006.01) | |
| A61K 8/36 | (2006.01) | |
| A61K 8/49 | (2006.01) | |
| A61Q 17/00 | (2006.01) | |
| A61Q 5/02 | (2006.01) | |

(52) U.S. Cl.
CPC ................. *A61K 8/35* (2013.01); *A61K 8/31* (2013.01); *A61K 8/34* (2013.01); *A61K 8/361* (2013.01); *A61K 8/38* (2013.01); *A61K 8/49* (2013.01); *A61K 8/4973* (2013.01); *A61K 8/922* (2013.01); *A61Q 5/006* (2013.01); *A61Q 15/00* (2013.01); *C11B 9/0015* (2013.01); *C11B 9/0046* (2013.01); *A61K 2800/75* (2013.01); *A61Q 5/02* (2013.01); *A61Q 17/005* (2013.01)

(58) Field of Classification Search
CPC .................................. A61K 36/28; A61K 36/00
USPC ........................................................ 424/725
See application file for complete search history.

(56) References Cited

U.S. PATENT DOCUMENTS

| | | | | |
|---|---|---|---|---|
| 2009/0285921 | A1* | 11/2009 | Kreuter .................. | A61K 36/28 424/764 |
| 2010/0104674 | A1* | 4/2010 | Jamel ..................... | A61K 36/28 424/764 |
| 2010/0124577 | A1* | 5/2010 | Jamel ..................... | A61K 8/97 424/764 |

FOREIGN PATENT DOCUMENTS

| | | |
|---|---|---|
| DE | 3300491 A1 | 7/1984 |
| WO | WO-2004/006876 A1 | 1/2004 |

OTHER PUBLICATIONS

Tuberoso et al. J. Agric. Food Chem. 2005. vol. 53, pp. 10148-10153.*
Smelcerovic et al. Chromatograhia. 2010. vol. 71, No. 1/2, pp. 113-116.*
Chaichat et al. J. Essential Oils Res. 1999. vol. 11, pp. 306-310.*
Bekhechi et al. J. Essential Oil Res., 2011. vol. 23, pp. 42-46.*
Bekhechi et al. J. Essential Oil Research. vol. 23, May/Jun. 2011, pp. 42-46.*
Suleimenov et al., "Essential Oil Composition of Three Species of *Achillea* From Kazakstan", Chemistry of Natural Compounds, vol. 37, No. 5, 2001.
Karamenderes et al., "Composition and antimicrobial activity of the essential oils of some *Achillea L.* Species in Turkey", Acta Pharmaceutica Turcica, 44:221-225 (2002).
Karamenderes et al., "Composition and antimicrobial activity of the essential oils of *Achillea nobilis L.* Subsp. *siplea* and Subsp. *neilreichii*", Chemistry of Natural Compounds, vol. 34, No. 5, pp. 632-634, 2007.
Baser et al., "Composition of the Essential Oils of Two Endemic Species from Turkey: *Achillea lycaonica* and *A. ketenoglui*", Chemistry of Natural Compounds, vol. 37, No. 3, pp. 245-252, 2001.
"Anti-Dandruff Shampoo", Mintel, Sep. 2009, XP002695943.

* cited by examiner

*Primary Examiner* — Michael V Meller
(74) *Attorney, Agent, or Firm* — Polsinelli PC

(57) ABSTRACT

The present invention relates to an *Achillea* essential oil comprising at least the following compounds, each preferably present in a proportion of at least 5% by weight, with respect to the total weight of the essential oil: artemisia ketone and chrysanthenone (two combined isomers). The invention also relates to a cosmetic composition comprising the said *Achillea* essential oil and to its cosmetic use as antidandruff agent or as deodorant active agent.

24 Claims, No Drawings

ACHILLEA ESSENTIAL OIL, COSMETIC COMPOSITION COMPRISING IT AND ITS USES

CROSS REFERENCE TO RELATED APPLICATIONS

This application is a National Phase filing under 35 U.S.C. § 371 of PCT/EP2013/056828 filed on Mar. 29, 2013; and this application claims priority to Application No. 1253815 filed in France on Apr. 25, 2012 and Application No. 1256877 filed in France on Jul. 17, 2012; and this application claims the benefit of U.S. Provisional Application No. 61/645,878 filed on May 11, 2012 and U.S. Provisional Application No. 61/727,142 on Nov. 16, 2012. The entire contents of each application are hereby incorporated by reference.

The present invention relates to a novel *Achillea* essential oil, to the cosmetic compositions comprising it and to the cosmetic use of the *Achillea* essential oil, in particular as antidandruff agent, especially in the cosmetic treatment of dandruff conditions related to the excessive proliferation of yeasts of the genus *Malassezia* on the scalp. The invention also relates to a cosmetic treatment method intended to eliminate and/or reduce dandruff, in particular that caused by yeasts of the genus *Malassezia*, which employs the said essential oil. The invention also relates to the use of the *Achillea* essential oil as deodorant active agent in a cosmetic composition.

Dandruff problems affect up to 50% of the world's population. They affect both men and women and are perceived as having a very negative psychosocial impact. The appearance of dandruff is disagreeable both aesthetically and because of the annoyance which it causes (in particular itching), so that many people confronted with this problem to variable degrees wish to be rid of it efficiently and permanently.

Dandruff corresponds to excessive and visible desquamation of the scalp resulting from the excessively rapid multiplication of the epidermal cells and from their abnormal maturation. This phenomenon can be brought about in particular by excessively aggressive hair treatments, extreme climatic conditions, nervousness, the diet, fatigue or pollution.

Dandruff conditions generally result from a disorder of the microflora of the scalp and more particularly from the excessive colonization by a fungi which belongs to the family of the yeasts of the genus *Malassezia* and which is naturally present on the scalp.

Many antidandruff treatments have been developed with the main objective of eradicating *Malassezia* yeasts from the scalp. Thus, the activity of the antidandruff active agents of today, such as zinc pyrithione, piroctone olamine or selenium di-sulfide, is based mainly on their fungicidal property. However, these anti-dandruff agents are not completely satisfactory in terms of effectiveness (immediate effectiveness or duration of the effect) and/or in terms of impact on the environment.

It is an aim of the present invention to provide an antidandruff agent which is non-irritating to the skin and scalp and which is more effective than the known antidandruff agents, while having a less unfavourable impact in terms of the environment (renewable starting materials which do not exhaust fossil resources and which do not pollute soils in biological cultivation, for example). Another aim of the invention is to provide an active agent which makes it possible to re-establish the ecoflora of the scalp and in particular to prevent excessive colonization of the scalp by *Malassezia* sp.

The Applicant Company has discovered, surprisingly, that the cosmetic use of an odorous *Achillea* essential oil makes it possible to effectively treat dandruff conditions, in particular those associated with the proliferation of yeasts of the genus *Malassezia*, and to overcome the disadvantages of the prior art. It has been observed that, by employing the essential oil according to the invention, it is possible to remove and/or reduce the number of yeasts of the genus *Malassezia*, the amount of dandruff, and the itching and redness of the scalp.

A first subject-matter of the invention is thus an *Achillea* essential oil comprising the following compounds, each preferably present in a proportion of at least 5% by weight, with respect to the total weight of the essential oil: artemisia ketone and chrysanthenone (two combined isomers).

The present invention also relates to a cosmetic composition comprising the said *Achillea* essential oil.

Another subject-matter of the invention is the cosmetic use of the said *Achillea* essential oil or of a cosmetic composition comprising it as antidandruff agent.

Furthermore, it is known that the unpleasant odours of perspiration are related in particular to the presence of microorganisms and more particularly *Corynebacterium xerosis*. In fact, sweat is in itself relatively non-odorous when it is secreted. It is the decomposition by bacteria via enzymatic reactions which produces malodorous compounds. Deodorant active agents have the specific function of reducing or preventing the formation of unpleasant odours.

The various systems proposed to date can be combined into main families: mention may be made of (i) antibacterial substances which destroy the resident bacterial flora, the most widely employed being triclosan, and (ii) substances which reduce the growth of the bacteria; mention may be made of chelating agents for transition metals, such as EDTA or diethylenetriaminepentaacetic acid (DTPA).

However, these various treatments, applied to the skin of the armpits, have a tendency to bring about detrimental changes in the skin.

The need thus remains to find novel deodorant active agents which are effective and which do not exhibit these disadvantages.

The activity as deodorant active agent of the *Achillea* essential oil according to the invention has thus been demonstrated, which makes it possible to confer on it usefulness in a deodorant cosmetic composition.

The term "deodorant active agent" is understood to mean, in the context of the present invention, any active agent which, by itself alone, has the effect of masking, absorbing, improving and/or reducing the unpleasant odour resulting from the decomposition of human sweat.

The term "antiperspirant active agent" is understood to mean any substance which, by itself alone, has the effect of reducing the flow of sweat, of reducing the sensation on the skin of moisture associated with human sweat and of masking human sweat.

Another subject-matter of the present invention is thus the cosmetic use of the said *Achillea* essential oil or of a cosmetic composition comprising it as deodorant active agent.

In the present invention, the term "keratinous substance" is understood in particular to mean the skin (face, body, scalp), hair, eyelashes, eyebrows and nails.

Within the meaning of the present invention, the term "physiologically acceptable medium" is understood to mean a medium which is suitable for the topical administration of a composition.

A physiologically acceptable medium is preferably a cosmetically or pharmaceutically acceptable medium, that is to say a medium which is devoid of unpleasant odour or appearance and which is entirely compatible with the topical administration route.

In the present case, where the composition is intended for topical administration, that is to say for administration by application at the surface of the keratinous substance under consideration, such a medium is considered in particular to be physiologically acceptable when it does not cause stinging, tightness or redness unacceptable to the user.

According to the definition given in the international standard ISO 9235 and adopted by the Commission of the European Pharmacopoeia, an essential oil is an odorous product, generally of complex composition, obtained from a botanically defined plant starting material, either by steam distillation, or by dry distillation, or by an appropriate mechanical process without heating (cold expression). The essential oil is generally separated from the aqueous phase by a physical process which does not result in any significant change in the composition.

Essential oils are generally volatile and liquid at ambient temperature (25° C.), which distinguishes them from "fixed" oils. They are more or less coloured and their density is generally less than that of water. They have a high refractive index and most of them deflect polarized light. They are liposoluble and soluble in the usual organic solvents, steam distillable and very sparingly soluble in water.

The *Achilleae* are plants of the family of the Asteraceae. These plants are present naturally in the southern half of the Drôme. For some years, these plants have been adapting to the local biotope since they are colonizing the taluses on the edge of the plateau of Les Chaux on the site of Gigors-et-Lozeron.

Mention may be made, as examples of *Achillea* essential oils capable of being used according to the invention, of those extracted from at least one of the following plants: *Achillea odorata, Achillea distans, Achillea collina, Achillea ageratum, Achillea ligustica, Achillea asplen, Achillea millefolium* and in particular *Achillea millefolium* subsp. *Pannonica* and *Achillea millefolium* subsp. *Millefolium, Achillea crithmifolia* and *Achillea kotschyi* subsp. *Kotschyu*.

Preferably, the *Achillea* essential oils are extracted from *Achillea odorata L.* or from *Achillea crithmifolia*, more particularly from *Achillea odorata L.* The *Achillea* essential oil extracted from *Achillea crithmifolia* is described in particular under the name crithmifolia Waldst. & Kitt in the document by Canan Karamenderes et al., *Acta Pharmaceutica Turcica*, 44, 221-225 (2002).

Preferably, the *Achillea* essential oil capable of being used according to the invention comprises the following compounds, each preferably present in a proportion of at least 5% by weight, with respect to the total weight of the essential oil: artemisia ketone and chrysanthenone (two combined isomers).

Preferably, it additionally comprises the following compound, preferably present in a proportion of at least 5% by weight, with respect to the total weight of the essential oil: ascaridole.

More particularly, in the *Achillea* essential oil according to the invention, these three compounds are each present at at least 6% by weight, with respect to the total weight of the essential oil.

The *Achillea* essential oil according to the invention can additionally comprise the following compounds, each preferably present at a content of 3% to 10% by weight, with respect to the total weight of the essential oil:
α-thujone,
para-cymene,
1,8-cineole and β-phellandrene, and
camphor.

The essential oil according to the invention can also comprise the following compounds, each preferably present at a content of less than 3% by weight, in particular of between 1% and 3% by weight, with respect to the total weight of the essential oil:
camphene,
yomogi alcohol,
cis-chrysanthenol,
artemisyl acetate, and
isoascaridole.

The *Achillea* essential oil according to the invention can advantageously be obtained from the aerial part of the plant. Harvesting can be carried out at different stages of cutting: beginning of flowering or end of flowering and preferably at the end-of-flowering stage.

The choice of the technique for obtaining an essential oil depends mainly on the starting material: its original state and its characteristics, its nature proper. The "essential oil/plant starting material" yield can be extremely variable depending on the plants: from 15 ppm to more than 20%. This choice conditions the characteristics of the essential oil, in particular viscosity, colour, solubility, volatility, and richness or poorness in certain constituents.

Mention may be made, among the methods for obtaining an essential oil, of steam distillation, which can, for example, be carried out by dry distillation or hydrodistillation.

Hydrodistillation can be carried out on a glass apparatus, such as that defined in the European Pharmacopoeia for the determination of the essential oil from a plant material.

Steam distillation corresponds to the vaporization, in the presence of steam, of a substance which is not very miscible with water The starting material is brought together with water brought to boiling point (hydrodistillation) or with steam in a still (dry distillation). The steam entrains the essential oil vapour, which is condensed in the condenser in order to be recovered as liquid phase in a Florentine flask (or essence jar), where the essential oil is separated from the water by settling. The term "aromatic water" or "hydrolat" or "distilled floral water" is used to describe the aqueous distillate which remains after the steam distillation, once the essential oil has been separated.

The chemical composition of the *Achillea* essential oil according to the invention thus obtained can be analysed by conventional techniques known to a person skilled in the art, such as gas chromatography GC analysis, chromatographic analysis with flame ionization detection, referred to as GC-FID, or GC/MS analysis, which consists of the use of a mass spectrometer coupled to a gas chromatograph.

The *Achillea* essential oil according to the invention can advantageously be obtained from the aerial part of the plant, in particular from *Achillea odorata L.* or from any other *Achillea* species or subspecies providing an essential oil comprising the following compounds, each present in a proportion of at least 5% by weight, with respect to the total weight of the essential oil: artemisia ketone and chrysanthenone (two combined isomers); and preferably additionally comprising the following compound, present in a proportion of at least 5% by weight, with respect to the total weight of the essential oil: ascaridole. An essential oil obtained from the aerial part of *Achillea odorata* L., generally called odorous *Achillea* essential oil, is particularly preferred in the context of the invention.

The cosmetic composition can comprise the *Achillea* essential oil at a content of between 0.001% and 5%, in particular between 0.01% and 3%, more particularly between 0.05% and 2% and better still between 0.1% and 1% by weight, with respect to the total weight of the composition.

The cosmetic compositions capable of being used in the context of the invention generally comprise a cosmetically acceptable medium, that is to say a medium compatible with keratinous substances, such as the skin of the face or body, the hair, the eyelashes, the eyebrows and the nails.

The cosmetic composition can be anhydrous or can comprise, preferably, an aqueous or aqueous/organic medium; it can thus comprise water and/or one or more organic solvents which can be chosen from linear or branched $C_1$-$C_6$ monoalcohols, such as ethanol, isopropanol, tert-butanol or n-butanol; polyols, such as glycerol, polypropylene glycol, hexylene glycol (or 2-methyl-2,4-pentanediol) and polyethylene glycols; polyol ethers, such as dipropylene glycol monomethyl ether; and their mixtures.

Preferably, the cosmetic composition comprises an amount of organic solvents ranging from 0.05% to 60%, preferably from 0.5% to 50% and better still from 1% to 40% by weight, with respect to the total weight of the cosmetic composition.

According to one embodiment, the cosmetic composition can be an aqueous composition. The term "aqueous" is understood to mean a composition for which the content of free water is greater than 10% by weight, preferably greater than 30% by weight, better still greater than 50% by weight and indeed even greater than 70% by weight, with respect to the total weight of the composition.

According to another embodiment, the cosmetic composition can be an anhydrous composition. The term "anhydrous" is understood to mean a composition for which the content of free or added water is less than 10% by weight, in particular less than 3% by weight, and preferably for which the content of added water is less than 1% by weight, with respect to the total weight of the composition. Preferably, the anhydrous cosmetic composition does not comprise water.

When the cosmetic composition according to the invention is intended for an anti-dandruff application, it can be a rinse-off or leave-on composition. The said composition, in particular hair composition, is then preferably a shampoo, a cream, a foam (aerosol or non-aerosol), a paste, a gel, an emulsion, a lotion or a stick. Preferably, the cosmetic composition is provided in the form of a shampoo, of a gel or of a lotion, in particular having an antidandruff effect.

The cosmetic composition can then advantageously comprise at least one additional constituent normal in cosmetics, such as, in particular, thickeners; surfactants chosen from anionic, cationic, non-ionic, amphoteric and/or zwitterionic surfactants; conditioning agents; silicones; agents for combating hair loss; other anti-dandruff agents; vitamins; waxes; sunscreens; coloured or colourless inorganic or organic pigments; dyes; pearlescent and opacifying agents; sequestering agents; plasticizing agents; fragrances; or preservatives. Of course, a person skilled in the art will take care to choose this or these optional additional compounds and/or their amounts in such a way that the advantageous properties of the composition according to the invention are not, or not substantially, detrimentally affected by the envisioned addition.

The cosmetic composition may or may not be rinsed off after having been applied to the keratinous substances (hair and/or scalp).

Furthermore, after the application of the cosmetic composition according to the invention, it is possible to apply, to the surface of the keratinous substances, a composition comprising one or more active agents chosen from antibacterials, antifungals and/or powders.

A further subject-matter of the invention is a cosmetic treatment method intended to eliminate and/or reduce dandruff, in particular that brought about by yeasts of the genus *Malassezia*, characterized in that it comprises the application, to the hair and/or scalp, of at least one *Achillea* essential oil according to the invention or of a cosmetic composition comprising it.

The stage of application of the said oil or of the composition comprising it may or may not be followed by a stage of rinsing with water.

Preferably, this cosmetic treatment method is repeated at the rate of at least twice weekly.

When the cosmetic composition according to the invention is intended for a deodorant application, it is provided in the form of a deodorant composition and can comprise other essential oils, such as basil, lemon catnip, citronella, clove, geranium, litsea cubeba, lemon balm, oregano and thyme essential oils. It can also comprise at least one additional deodorant active agent and/or an antiperspirant active agent as defined below.

The composition according to the invention can comprise one or more additional deodorant active agents, such as:

bacteriostatic agents or bactericidal agents, such as 2,4,4'-trichloro-2'-hydroxydiphenyl ether (triclosan), 2,4-dichloro-2'-hydroxydiphenyl ether, 3',4',5'-trichlorosalicylanilide, 1-(3',4'-dichlorophenyl)-3-(4'-chlorophenyl)urea (triclocarban) or 3,7,11-trimethyldodeca-2,5,10-trienol (farnesol); quaternary ammonium salts, such as cetyltrimethylammonium salts or cetylpyridinium salts; chlorhexidine and its salts; diglyceryl monocaprate, diglyceryl monolaurate, glyceryl monolaurate; polyhexamethylene biguanide salts;

zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc lactate, zinc acetate or their mixtures;

odour absorbers, such as zeolites, cyclodextrins, metal oxide silicates, such as those described in Application U.S. 2005/063 928, metal oxide particles modified by a transition metal, such as described in Applications U.S. 2005/084 464 and U.S. 2005/084 474, aluminosilicates, such as those described in Application EP 1 658 863, or particles of chitosan derivatives, such as those described in U.S. Pat. No. 6,916,465;

substances which block the enzymatic reactions responsible for the formation of odorous compounds, such as arylsulfatase, 5-lipoxygenase, aminocylase or β-glucuronidase inhibitors;

and their mixtures.

The deodorant active agents can be present in the composition according to the invention in a proportion of from 0.01% to 10% by weight and preferably in a proportion of from 0.1% to 5% by weight, with respect to the total weight of the composition.

The antiperspirant active agents are preferably chosen from aluminium and/or zirconium salts; complexes of zirconium hydroxychloride and of aluminium hydroxychloride with an amino acid, such as those described in U.S. Pat. No. 3,792,068, commonly known as "ZAG" complexes. Such complexes are generally known under the name ZAG (when the amino acid is glycine). The ZAG complexes ordinarily exhibit an Al/Zr quotient ranging from approximately 1.67 to 12.5 and a metal/CI quotient ranging from approximately 0.73 to 1.93. Mention may be made, among these products, of aluminium zirconium octachlorohydrex GLY, aluminium zirconium pentachlorohydrex GLY, aluminium zirconium tetrachlorohydrate GLY and aluminium zirconium trichlorohydrate GLY.

Mention may be made, among the aluminium salts, of aluminium chlorohydrate, aluminium chlorohydrex, aluminium chlorohydrex PEG, aluminium chlorohydrex PG, aluminium dichlorohydrate, aluminium dichlorohydrex PEG, aluminium dichlorohydrex PG, aluminium sesquichlorohydrate, aluminium sesquichlorohydrex PEG, aluminium sesquichlorohydrex PG, alum salts, aluminium sulfate, aluminium zirconium octachlorohydrate, aluminium zirconium pentachlorohydrate, aluminium zirconium tetrachlorohydrate, aluminium zirconium trichlorohydrate and more particularly the aluminium hydroxychloride sold by Reheis under the name Reach 301 or by Guilini Chemie under the name Aloxicoll PF 40. Mention may be made, among the aluminium zirconium salts, of that sold by Reheis under the name Reach AZP-908-SUF.

Use will more particularly be made of aluminium chlorohydrate in the activated or non-activated form.

The antiperspirant active agents can be present in the composition according to the invention in a proportion of from 0.001% to 30% by weight and preferably in a proportion of from 0.5% to 25% by weight, with respect to the total weight of the composition.

The composition according to the invention can be provided in any formulation form conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semi-liquid consistency of the milk type, obtained by dispersion of a fatty phase in an aqueous phase (O/W) or vice versa (W/O), or of suspensions or emulsions with a soft, semi-solid or solid consistency of the cream or gel type, or alternatively of multiple emulsions (W/O/W or O/W/O), of microemulsions, of vesicular dispersions of ionic and/or non-ionic type, or of wax/aqueous phase dispersions. The compositions can in particular be packaged in the pressurized form in an aerosol device or in a pump-action spray; packaged in a device equipped with an openwork wall, in particular a grating; packaged in a device equipped with a ball applicator ("roll-on"); packaged in the form of a stick (solid composition) or in the form of a loose or compacted powder.

In this regard, they comprise the ingredients generally used in products of this type and which are well-known to a person skilled in the art, chosen in particular from oil-in-water or water-in-oil emulsifiers; volatile or non-volatile oils; structuring agents; waxes, pasty compounds or inorganic or organic lipophilic gelling agents; softeners, antioxidants, opacifiers, stabilizing agents, moisturizing agents, vitamins, preservatives, polymers, fragrances, powders, in particular organic powders, thickeners or suspending agents. Of course, a person skilled in the art will take care to choose this or these optional additional compounds in such a way that the advantageous properties intrinsically attached to the cosmetic composition in accordance with the invention are not, or not substantially, detrimentally affected by the envisaged addition or additions.

The compositions according to the invention can optionally be pressurized and be packaged in an aerosol device composed of a container comprising a composition as defined above and at least one propellant and a means for dispensing the said aerosol composition.

The propellants can be chosen in particular from carbon dioxide gas, nitrous oxide, nitrogen, compressed air, dimethyl ether (DME) or volatile hydrocarbons, such as n-butane, propane, isobutane and their mixtures, optionally with at least one chlorinated and/or fluorinated hydrocarbon, such as monofluorotrichloromethane, di-fluorodichloromethane, tetrafluorodichloroethane and 1,1-difluoroethane.

Thus, the invention also relates to a cosmetic method for treating human body odours, in particular of the armpits or feet, which consists in applying, to human keratinous substances, an *Achillea* essential oil according to the invention or a cosmetic composition comprising it.

The invention also relates to a cosmetic composition packaged in the pressurized form in an aerosol device or in a pump-action spray, in a device equipped with an openwork wall, in particular a grating, in a device equipped with a ball applicator ("roll-on"), in the form of a stick or in the form of a loose or compacted powder, characterized in that it comprises *Achillea* essential oil as defined above.

The invention is illustrated in greater detail in the following examples.

EXAMPLE 1

An odorous *Achillea* essential oil was prepared by distillation of 300 g of fresh aerial part, collected at the deblossomed stage, of *Achillea odorata* in an apparatus of Clevenger type, by dry distillation for 90 minutes. An essential oil was obtained with a yield of the order of 0.25% to 0.50%.

The essential oil thus obtained comprises:

| | |
|---|---|
| *Artemisia* ketone | 33.4% |
| Ascaridole | 11.70% |
| Chrysanthenone | 6.6% |
| 1,8-Cineole and β-phellandrene | 6.3% |
| para-Cymene | 5.7% |
| Camphor | 5.3% |
| α-Thujone | 4.3% |
| Yomogi alcohol | 1.3% |
| Artemisyl acetate | 1.3% |
| Camphene | 1.2% |
| Isoascaridole | 1.0% |

The composition of the essential oil obtained was determined by GC and mass spectrometry.

EXAMPLE 2

Activity Tests
Principle
By a method of dilution in a liquid medium, bringing different concentrations of product into contact with a nutritive broth inoculated with the test strain. After incubation, counting the surviving microorganisms (log).

Protocol preparation of the test product: a 10% (w/v) stock solution in 1‰ agar is prepared; after stirring, dilutions are carried out in order to prepare 0.02%, 0.1%, 0.2%, 1% and 2% (w/v) solutions.

bringing the product into contact, at a concentration double the test concentration, with a doubly concentrated nutritive broth assaying approximately between 2 and $6.10^5$ CFU/ml.

after incubating at 32.5° C.±2.5° C. for 24 h, the surviving microorganisms are counted by spiral inoculation and compared with the starting inoculum in order to define the degrees of reduction obtained. A value of 5 log is assigned to the initial inoculum.

Spiral inoculation systems use a semi-automatic inoculater, which deposits a calibrated volume of a liquid sample at the surface of an agar placed on a rotating plate, while describing an Archimedean spiral. After incubation, reading is carried out using graphs. This technique makes it possible to carry out the bacterial count of a sample on one and the same dish, dispensing with all or some of the intermediate dilutions. This methodology is much used and is an officially accepted technique.

Operating Conditions concentrations of test product: 0.01%, 0.05%, 0.1%, 0.5% and 1% (w/v)

diluant used: 1‰ agar appearance in the broth: opaque emulsion

Results on *Pityrosporum Ovale*

After having inoculated 6.7 log in the medium comprising different concentrations of the essential oil, a decrease in the population of 3.2 log is observed from 0.5% and complete decontamination of the microbial population is observed after 24 hours at 1%.

| | *Pityrosporum ovale* | | | | |
|---|---|---|---|---|---|
| | 0.01% | 0.05% | 0.1% | 0.5% | 1% |
| Odorous *Achillea* essential oil (Example 1) | 6.2 | 5.6 | 5.5 | 3.5 | 0 |

Results on *Corynebacterium Xerosis*

After having inoculated approximately 5 log of Corynebacterium xerosis (CIP 5216—Institut Pasteur) in the medium comprising different concentrations of the essential oil, a decontamination of the order of 2 log of the bacterial population is obtained after 24 hours, from 0.5% (w/v), and then of more than 3 log from 1% (w/v).

| | *Corynebacterium xerosis* | | |
|---|---|---|---|
| | 0.1% | 0.5% | 1% |
| Odorous *Achillea* essential oil (Example 1) | 5.04 | 3.08 | 1.6 |

EXAMPLE 3

An antidandruff shampoo is prepared, comprising (% by weight):

| | |
|---|---|
| Sodium Laureth Sulfate | 12% |
| Disodium Cocoamphodiacetate | 3.5% |
| Odorous *Achillea* essential oil (Example 1) | 0.5% |
| Glycol Distearate | 2% |

| | |
|---|---|
| Cocamide MIPA (and) Isopropanolamine | 1.5% |
| Salicylic Acid | 0.5% |
| Piroctone Olamine | 0.5% |
| HCl | q.s. pH 7 |
| Water | q.s. for 100% |

EXAMPLE 4

A deodorant composition in the form of an aerosol is prepared, comprising (% by weight):

| | |
|---|---|
| Essential oil according to Example 1 | 0.5% |
| Triclosan | 0.75% |
| Silicone | 3% |
| Fragrance | 0.75% |
| Isobutane and propane | 45% |
| Ethyl alcohol | q.s. for 100% |

EXAMPLE 5

An antiperspirant and deodorant composition in the form of a roll-on is prepared, comprising (% by weight):

| | |
|---|---|
| Essential oil according to Example 1 | 0.5% |
| Aluminium Chlorohydrate | 25% |
| PPG-15 Stearyl Ether | 2% |
| Silicone | 1.25% |
| Ceteareth-33 | 2% |
| Fragrance | 0.7% |
| Water | q.s. for 100% |

The invention claimed is:

1. A cosmetic composition capable of use as an antidandruff composition or deodorant composition consisting essentially of an *Achillea* essential oil comprising the following compounds: artemisia ketone in a proportion of 5% to 33.4% by weight, with respect to the total weight of the essential oil, chrysanthenone in a proportion of 5% to 6.6% by weight, with respect to the total weight of the essential oil or chrysanthenone and its isomer verbenone in a combined proportion of 5% to 6.6% by weight, with respect to the total weight of the essential oil, and ascaridole in a proportion of 5% to 11.7% by weight, with respect to the total weight of the essential oil and a cosmetically or pharmaceutically acceptable medium which is compatible with topical administration of the cosmetic composition and wherein the *Achillea* essential oil is at a content of between 0.001% and 5% by weight with respect to the total weight of the cosmetic composition; wherein the cosmetic composition is in a form selected from the group consisting of an emulsion, packaged in a pressurized device, packaged in an aerosol device, packaged in a pump-action spray device, packaged in a device equipped with a ball applicator and mixtures thereof.

2. The cosmetic composition of claim 1, wherein the at least one *Achillea* essential oil additionally comprises the following compounds, each present at a content of 3% to 10% by weight, with respect to the total weight of the essential oil:
 α-thujone,
 para-cymene,
 1,8-cineole,
 β-phellandrene and
 camphor.

3. The cosmetic composition of claim 1, wherein the at least one *Achillea* essential oil additionally comprises the following compounds, each present at a content of less than 3% by weight with respect to the total weight of the essential oil:
camphene,
yomogi alcohol,
cis-chrysanthenol,
artemisyl acetate, and
isoascaridole.

4. The cosmetic composition of claim 1, wherein the at least one *Achillea* essential oil comprises the following compounds: artemisia ketone in a proportion of at least 6% by weight, with respect to the total weight of the essential oil, chrysanthenone in a proportion of 5% to 6.6% by weight, with respect to the total weight of the essential oil or chrysanthenone and its isomer verbenone in a combined proportion of 5% to 6.6% by weight, with respect to the total weight of the essential oil and ascaridole in a proportion of at least 6% by weight, with respect to the total weight of the essential oil.

5. The cosmetic composition of claim 1, wherein the at least one *Achillea* essential oil is extracted from a plant selected from the group consisting of *Achillea odorata, Achillea distans, Achillea collina, Achillea ageratum, Achillea ligustica, Achillea asplen, Achillea millefolium* and mixtures thereof.

6. The cosmetic composition of claim 1, which is an aqueous or anhydrous composition.

7. The cosmetic composition of claim 1, which is a deodorant composition comprising the at least one *Achillea* essential oil in a deodorant active amount and wherein the at least one *Achillea* essential oil is effective against *Corynebacterium xerosis*.

8. The cosmetic composition of claim 1, packaged in a pressurized form in an aerosol device or packaged in a pump-action spray device.

9. The cosmetic composition of claim 2, wherein the at least one *Achillea* essential oil additionally comprises the following compounds, each present at a content of less than 3% by weight with respect to the total weight of the essential oil:
camphene,
yomogi alcohol,
cis-chrysanthenol,
artemisyl acetate, and
isoascaridole.

10. The cosmetic composition of claim 2, wherein the at least one *Achillea* essential oil comprises the following compounds: artemisia ketone in a proportion of at least 6% by weight, with respect to the total weight of the essential oil, chrysanthenone in a proportion of 5% to 6.6% by weight, with respect to the total weight of the essential oil or chrysanthenone and its isomer verbenone in a combined proportion of 5% to 6.6% by weight, with respect to the total weight of the essential oil and ascaridole in a proportion of at least 6% by weight, with respect to the total weight of the essential oil.

11. The cosmetic composition of claim 3, wherein the at least one *Achillea* essential oil additionally comprises the following compounds: artemisia ketone in a proportion of at least 6% by weight, with respect to the total weight of the essential oil, chrysanthenone in a proportion of 5% to 6.6% by weight, with respect to the total weight of the essential oil or chrysanthenone and its isomer verbenone in a combined proportion of 5% to 6.6% by weight, with respect to the total weight of the essential oil and ascaridole in a proportion of at least 6% by weight, with respect to the total weight of the essential oil.

12. The cosmetic composition of claim 11, wherein the at least one *Achillea* essential oil is obtained from the aerial part of *Achillea odorata L.*

13. The cosmetic composition of claim 10, wherein the at least one *Achillea* essential oil is obtained from the aerial part of *Achillea odorata L.*

14. The cosmetic composition of claim 1, wherein the at least one essential oil is obtained from the aerial part of *Achillea odorata L.*

15. The cosmetic composition of claim 7, packaged in a device equipped with a ball applicator.

16. The cosmetic composition of claim 1, which is a antidandruff composition comprising the at least one *Achillea* essential oil in an antidandruff active amount and wherein the at least one *Achillea* essential oil is effective against excessive colonization of the scalp by *Malassezia* sp.

17. The cosmetic composition of claim 7, packaged in an aerosol device.

18. The cosmetic composition of claim 1, wherein the *Achillea* essential oil is between 0.01% and 3% by weight with respect to the total weight of the cosmetic composition.

19. The cosmetic composition of claim 1, wherein the *Achillea* essential oil is between 0.1% and 1% by weight with respect to the total weight of the cosmetic composition.

20. The cosmetic composition of claim 1, which further comprises a component selected from the group consisting of thickeners; surfactants; conditioning agents; silicones; agents for combating hair loss; other antidandruff agents; vitamins; waxes; sunscreens; inorganic or organic pigments; dyes; pearlescent and opacifying agents; sequestering agents; plasticizing agents; fragrances; preservatives; other essential oils; additional deodorant active agents and antiperspirant active agents.

21. The cosmetic composition of claim 20, which is in the form of being packaged in a device equipped with a ball applicator.

22. The cosmetic composition of claim 20, which is a deodorant composition comprising the at least one *Achillea* essential oil in a deodorant active amount and wherein the at least one *Achillea* essential oil is effective against *Corynebacterium xerosis*.

23. The cosmetic composition of claim 1, which is an emulsion.

24. The cosmetic composition of claim 1, packaged in a device equipped with a ball applicator.

* * * * *